(12) United States Patent
Song et al.

(10) Patent No.: US 12,070,355 B2
(45) Date of Patent: Aug. 27, 2024

(54) ULTRASOUND DIAGNOSTIC APPARATUS AND METHOD OF CONTROLLING THE SAME

(71) Applicant: SAMSUNG MEDISON CO., LTD., Gangwon-do (KR)

(72) Inventors: Chang Wook Song, Seoul (KR); Kyeong Gu Woo, Suwon-si (KR); Gil Ju Jin, Seoul (KR)

(73) Assignee: SAMSUNG MEDISON CO. LTD., Gangwon-Do (KR)

(*) Notice: Subject to any disclaimer, the term of this patent is extended or adjusted under 35 U.S.C. 154(b) by 0 days.

(21) Appl. No.: 17/831,880

(22) Filed: Jun. 3, 2022

(65) Prior Publication Data
US 2022/0304657 A1 Sep. 29, 2022

Related U.S. Application Data

(63) Continuation of application No. 16/776,093, filed on Jan. 29, 2020, now Pat. No. 11,375,977.

(30) Foreign Application Priority Data

Feb. 15, 2019 (KR) .......................... 10-2019-0017988

(51) Int. Cl.
*A61B 8/00* (2006.01)
*B60B 33/00* (2006.01)
*B62B 5/04* (2006.01)

(52) U.S. Cl.
CPC .......... *A61B 8/4405* (2013.01); *A61B 8/4254* (2013.01); *A61B 8/462* (2013.01);
(Continued)

(58) Field of Classification Search
CPC ..... A61B 8/4405; A61B 8/4254; A61B 8/462; A61B 8/467; A61B 8/54; A61B 8/461;
(Continued)

(56) References Cited

U.S. PATENT DOCUMENTS 10,145,946 B2* 12/2018 Kashima ................ A61B 8/462
10,160,262 B2* 12/2018 Hein ..................... B60B 33/021
(Continued)

FOREIGN PATENT DOCUMENTS

EP 2620293 A1 7/2013
EP 2891969 * 12/2014
(Continued)

OTHER PUBLICATIONS

U.S. Notice of Allowance dated Mar. 8, 2022 issued in U.S. Appl. No. 16/776,093.
(Continued)

*Primary Examiner* — Alexei Bykhovski
(74) *Attorney, Agent, or Firm* — Morgan, Lewis & Bockius LLP

(57) ABSTRACT

Provided is an ultrasound diagnostic apparatus including a plurality of casters allowing the ultrasound diagnostic apparatus to be moved according to a control signal, a detection sensor configured to detect a motion of the ultrasound diagnostic apparatus, an input configured to receive a control command of the ultrasound diagnostic apparatus from a user, and a controller configured to determine whether a user desires to use the ultrasound diagnostic apparatus on the basis of at least one of the detected motion or the received control command, and upon determining that the user desires to use the ultrasound diagnostic apparatus, transmit a control signal for locking at least one of the plurality of casters.

18 Claims, 12 Drawing Sheets

(52) U.S. Cl.
CPC .............. *A61B 8/467* (2013.01); *A61B 8/54* (2013.01); *B60B 33/0086* (2013.01); *B60B 33/0094* (2013.01); *B62B 5/0404* (2013.01)

(58) Field of Classification Search
CPC . A61B 8/4245; A61B 8/4444; B60B 33/0086; B60B 33/0094; B62B 5/0404
See application file for complete search history.

(56) References Cited

U.S. PATENT DOCUMENTS

| | | | | |
|---|---|---|---|---|
| 2005/0113684 | A1* | 5/2005 | Lokhandwalla | G01H 3/00 128/915 |
| 2016/0157818 | A1* | 6/2016 | Cho | A61B 8/4444 600/443 |
| 2016/0183920 | A1* | 6/2016 | Woo | A61B 8/461 600/440 |
| 2016/0200336 | A1* | 7/2016 | Woo | B62B 5/00 280/86.751 |
| 2017/0087730 | A1 | 3/2017 | Robinson et al. | |
| 2018/0235580 | A1* | 8/2018 | Park | G01S 15/8979 |
| 2018/0294052 | A1 | 10/2018 | Fishman | |

FOREIGN PATENT DOCUMENTS

| | | |
|---|---|---|
| EP | 2977012 A1 | 1/2016 |
| JP | 2008-067794 A | 3/2008 |
| JP | 5204688 B2 | 2/2013 |
| JP | 5834275 B1 | 12/2015 |
| KR | 10-2018-0090556 A | 8/2018 |
| WO | WO2013142896 * | 10/2013 |

OTHER PUBLICATIONS

U.S. Final Office Action dated Nov. 2, 2021 issued in U.S. Appl. No. 16/776,093.
U.S. Non-Final Office Action dated May 11, 2021 issued in U.S. Appl. No. 16/776,093.
Extended European Search Report dated Jun. 9, 2020 issued in European Patent Application No. 20156817.7.
Korean Notice of Allowance dated Nov. 16, 2023 issued in Korean Patent Application No. 10-2019-0017988 (with English translation).

* cited by examiner

ULTRASOUND DIAGNOSTIC APPARATUS AND METHOD OF CONTROLLING THE SAME

CROSS-REFERENCE TO RELATED APPLICATION

This application is a Continuation patent application of U.S. patent application Ser. No. 16/776,093, filed on Jan. 29, 2020, which is based on and claims priority under 35 U.S.C. § 119 to Korean Patent Application No. 2019-0017988, filed on Feb. 15, 2019 in the Korean Intellectual Property Office, the disclosure of which is incorporated herein by reference.

BACKGROUND

1. Field

The disclosure relates to an ultrasound diagnostic apparatus for acquiring an image of an internal state of an object using ultrasound, and a method of controlling the same.

2. Description of the Related Art

Ultrasound diagnostic apparatuses operate to irradiate an ultrasound signal generated from a transducer of a probe to an object and receive an echo signal reflected from the object to acquire an image of the internal site of the object.

The ultrasound diagnostic apparatus has advantages in that it is inexpensive and moveable, is displayable in real time, and has high safety compared to X-ray diagnostic devices due to having no risk of exposure to X-rays or the like, and thus are widely used in a variety of fields, such as medical fields and the like.

Such a trend has led the ultrasound diagnostic apparatuses to be variously advanced, and increased the weight of the ultrasonic diagnostic apparatus, and thus when a user moves the ultrasonic diagnostic apparatus, a great amount of strength is required.

In order to remove such a limitation, various efforts have been conducted to minimize the force that the user takes to move the ultrasonic diagnostic apparatus by providing all canisters for movement of the ultrasound diagnostic apparatus to be independently moveable or replacing all the canisters with electric casters.

However, as the degree of freedom of movement of a control panel of the ultrasonic diagnostic apparatus increases, the electric caster operates with a high sensitivity, and thus even when a user desires to use the ultrasonic diagnostic apparatus, the ultrasonic diagnostic apparatus may be moved regardless of the user's intention.

SUMMARY

Therefore, it is an object of the disclosure to provide an ultrasound diagnostic apparatus capable of minimizing unneeded movement of the ultrasound diagnostic apparatus or preventing an accident due to an undesired movement of the ultrasound diagnostic apparatus by detecting a motion or input of a user and determining whether the user desires to use the ultrasound diagnostic apparatus on the basis of the detected motion or input and automatically locking casters of the ultrasound diagnostic apparatus.

Additional aspects of the disclosure will be set forth in part in the description which follows and, in part, will be obvious from the description, or may be learned by practice of the disclosure.

Therefore, it is an aspect of the disclosure to provide an ultrasound diagnostic apparatus including: a plurality of casters allowing the ultrasound diagnostic apparatus to be moved according to a control signal; a detection sensor configured to detect a motion of the ultrasound diagnostic apparatus; an input configured to receive a control command of the ultrasound diagnostic apparatus from a user; and a controller configured to determine whether a user desires to use the ultrasound diagnostic apparatus on the basis of at least one of the detected motion or the received control command, and upon determining that the user desires to use the ultrasound diagnostic apparatus, transmit a control signal for locking at least one of the plurality of casters.

The ultrasound diagnostic apparatus may include: a probe configured to radiate an ultrasound signal to an object and receive an ultrasound signal that is the ultrasound signal being radiated to the object, reflected from the object, wherein the controller may determine that the user desires to use the ultrasound diagnostic apparatus in response to detecting a position change of the probe.

The ultrasound diagnostic apparatus may further include: a monitor, wherein the controller may determine that the user desires to use the ultrasound diagnostic apparatus in response to detecting a position change of the monitor.

The ultrasound diagnostic apparatus may further include a control panel configured to control the ultrasound diagnostic apparatus, wherein the controller may determine that the user desires to use the ultrasound diagnostic apparatus in response to detecting a position change of the control panel.

The ultrasound diagnostic apparatus may further include a keyboard, wherein the controller may determine that the user desires to use the ultrasound diagnostic apparatus in response to detecting a position change of the keyboard.

The ultrasound diagnostic apparatus may further include a footrest on which a foot of the user is rested, wherein the controller may determine that the user desires to use the ultrasound diagnostic apparatus in response to detecting a position change of the footrest.

The controller may determine that the user desires to use the ultrasound diagnostic apparatus in response to receiving at least one of a unlock command for changing a position of a monitor or a diagnosis start command of the ultrasound diagnostic apparatus from the user.

The input may include a display provided in a monitor, wherein the controller may determine that the user desires to use the ultrasound diagnostic apparatus in response to the display receiving the control command from the user.

The input may include a trackball provided in a control panel, wherein the controller may determine that the user desires to use the ultrasound diagnostic apparatus in response to the trackball receiving the control command from the user.

The input may receive a unlock command for unlocking the plurality of casters from the user, wherein the controller may transmit a control signal for unlocking the plurality of casters in response to the input receiving the unlock command for the plurality of casters from the user.

The input may receive a command for activating or deactivating an auto lock function of the caster from the user, and in response to receiving the command for deactivating the auto lock function of the cast, the controller may prevent the control signal for locking the at least one of the plurality of casters even when it is determined that the user desires to use the ultrasound diagnostic apparatus The detection sensor may include at least one of a current sensor for detecting current generated by at least one of the detected motion or the received control command, or an acceleration sensor, a gyro sensor, or a motion sensor for detecting a movement generated by a motion of the ultrasound diagnostic apparatus.

It is another aspect of the disclosure to provide a method of controlling an ultrasound diagnostic apparatus, the method including: detecting a motion of the ultrasound diagnostic apparatus; receiving a control command of the ultrasound diagnostic apparatus from a user; determining whether a user desires to use the ultrasound diagnostic apparatus on the basis of at least one of the detected motion or the received control command; and upon determining that the user desires to use the ultrasound diagnostic apparatus, transmitting a control signal for locking at least one of the plurality of casters.

The determining of whether a user desires to use the ultrasound diagnostic apparatus on the basis of the detected motion may include determining that the user desires to use the ultrasound diagnostic apparatus in response to detecting a position change of the probe.

The determining of whether a user desires to use the ultrasound diagnostic apparatus on the basis of the detected motion may include determining that the user desires to use the ultrasound diagnostic apparatus in response to detecting a position change of the monitor.

The determining of whether a user desires to use the ultrasound diagnostic apparatus on the basis of the detected motion may include determining that the user desires to use the ultrasound diagnostic apparatus in response to detecting a position change of the control panel.

The determining of whether a user desires to use the ultrasound diagnostic apparatus on the basis of the detected motion may include determining that the user desires to use the ultrasound diagnostic apparatus in response to detecting a position change of the keyboard.

The determining of whether a user desires to use the ultrasound diagnostic apparatus on the basis of the detected motion may include determining that the user desires to use the ultrasound diagnostic apparatus in response to detecting a position change of the footrest.

The determining of whether a user desires to use the ultrasound diagnostic apparatus on the basis of the received control command may include determining that the user desires to use the ultrasound diagnostic apparatus in response to receiving at least one of a unlock command for changing a position of the monitor or a diagnosis start command of the ultrasound diagnostic apparatus from the user.

The determining of whether a user desires to use the ultrasound diagnostic apparatus on the basis of the received control command may include determining that the user desires to use the ultrasound diagnostic apparatus in response to the display receiving the control command from the user.

The determining of whether a user desires to use the ultrasound diagnostic apparatus on the basis of the received control command may include determining that the user desires to use the ultrasound diagnostic apparatus in response to the trackball receiving the control command from the user.

The method may further include receiving a unlock command for unlocking the plurality of casters from the user, and in response to receiving the unlock command, transmitting a control signal to unlock the plurality of casters.

The method may further include receiving a command for activating or deactivating an auto lock function of the caster from the user, and in response to receiving the command for deactivating the auto lock function of the cast, preventing the control signal for locking the at least one of the plurality of casters even when it is determined that the user desires to use the ultrasound diagnostic apparatus.

The detecting of the motion of the ultrasound diagnostic apparatus and the receiving of the control command of the ultrasound diagnostic apparatus from the user may include detecting current generated by at least one of the detected motion or the received control command.

The detecting of the motion of the ultrasound diagnostic apparatus may include detecting a change position of the ultrasound diagnostic apparatus that is generated by a motion of the ultrasound diagnostic apparatus.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
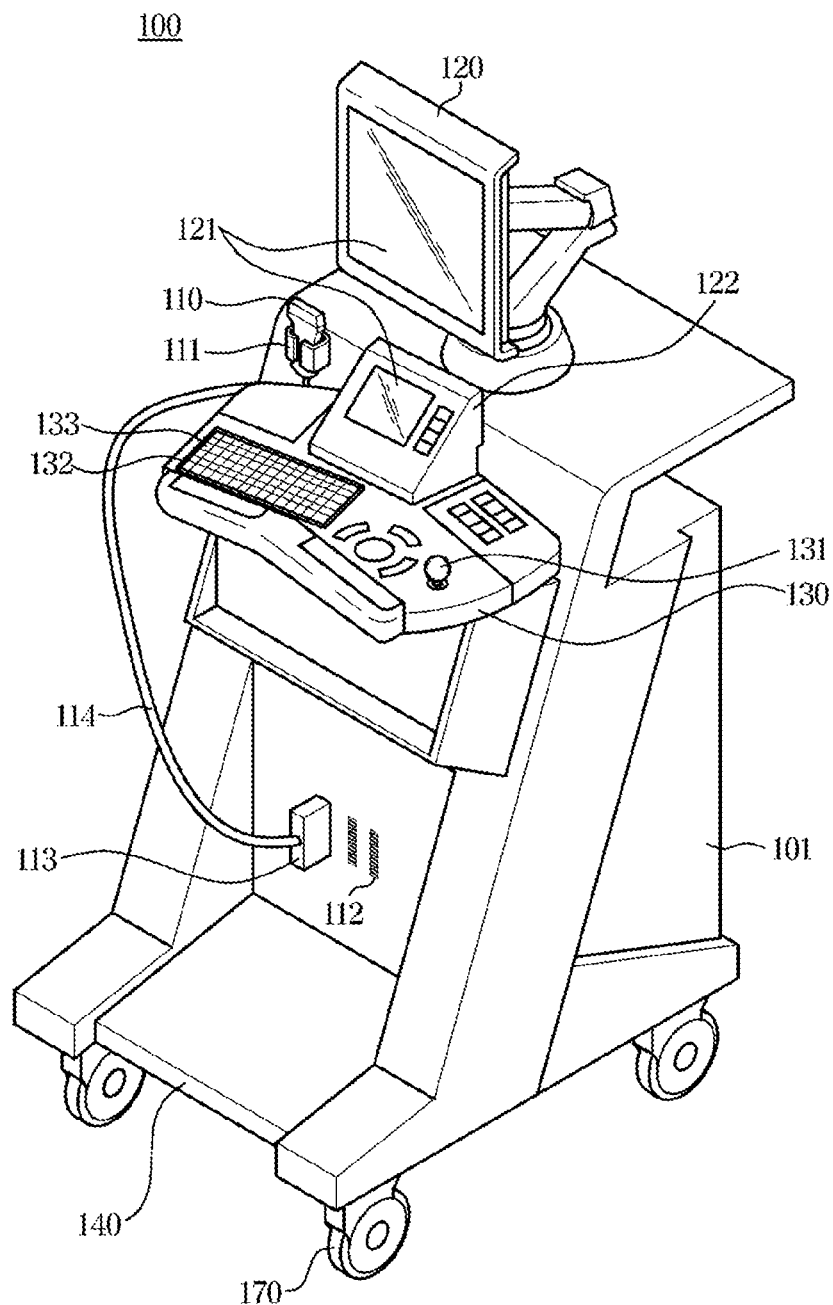
FIG. 1 is an external view illustrating an ultrasound diagnostic apparatus according to an embodiment.

Like numerals refer to like elements throughout the specification. Not all elements of embodiments of the disclosure will be described, and description of what are commonly known in the art or what overlap each other in the embodiments will be omitted. The terms as used throughout the specification, such as "~j part", "~j module", "~member", "~j block", etc., may be implemented in software and/or hardware, and a plurality of "~j parts", "~j modules", "~j members", or "~j blocks" may be implemented in a single element, or a single "~j part", "~j module", "~j member", or"~block" may include a plurality of elements.

It will be further understood that the term "connect" or its derivatives refer both to direct and indirect connection, and the indirect connection includes a connection over a wireless communication network.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, Further, it will be further understood when a signal or data is transferred, sent or transmitted from "an element" to "another element", it does not exclude another element between the element and the other element passed by the signal or data therethrough, unless the context clearly indicates otherwise.

Although the terms "first," "second," "A," "B," etc. may be used to describe various components, the terms do not limit the corresponding components, but are used only for the purpose of distinguishing one component from another component.

As used herein, the singular forms "a," "an" and "the" are intended to include the plural forms as well, unless the context clearly indicates otherwise.

Reference numerals used for method steps are just used for convenience of explanation, but not to limit an order of the steps. Thus, unless the context clearly dictates otherwise, the written order may be practiced otherwise.

Hereinafter, embodiments of an ultrasound diagnostic apparatus 100 according to an aspect and a method of controlling the same will be described with reference to the accompanying drawings in detail.

FIG. 1 is an external view illustrating an ultrasound diagnostic apparatus 100 according to an embodiment.

Referring to FIG. 1, the ultrasound diagnostic apparatus 100 according to the embodiment is an apparatus for displaying an ultrasound image by radiating an ultrasound signal to an object and receiving an ultrasound signal reflected from the object.

To this end, the ultrasound diagnostic apparatus 100 may include a probe 110 that radiates an ultrasound signal to an object and receives an ultrasound signal reflected on the object. A transducer module may be provided inside the ultrasound probe 110, and the ultrasound probe 110 may be connected to a main body 101 of the ultrasound diagnostic apparatus 100 through a cable 114.

To this end, the main body 101 may be provided at a front lower portion thereof with one or more female connectors 112. A male connector 113 provided at one end of the cable 114 may be physically coupled to the female connector 112.

One or more probe holders 111 for mounting the ultrasound probe 110 may be provided on an outer circumferential surface of the main body 101. Accordingly, when the user does not use the ultrasound probe 110, the user may store the ultrasound probe 110 on the probe holder 111.

A monitor 120 including a display 121 may be provided at an upper side of the main body 101. The display 121 may be implemented as at least one of various display panels, such as a liquid crystal display (LCD) panel, a light emitting diode (LED) panel, or an organic light emitting diode (OLED) panel.

In addition, the display 121 may be composed of two or more displays such that each display simultaneously displays a different image. For example, one display may display a 2D ultrasound image, and the other display may display a 3D ultrasound image. Alternatively, one display may display a B-mode image, and the other display may display a contrast agent image.

In addition, the ultrasound diagnostic apparatus 100 may further a sub monitor 122 that performs the same function as that of the monitor 120.

The main body 101 may be provided at a front surface with a control panel 130. An input 180 for receiving a user's input may be formed on the control panel 130 such that a user may input commands for starting a diagnosis, selecting a diagnosis site, selecting a diagnosis type, and selecting a mode of the ultrasound image. The mode of the ultrasound image may include an amplitude mode (A-mode), a brightness mode (B-mode), a doppler mode (D-mode), an elastography mode (E-mode), a motion mode (M-mode), and the like.

In addition, the input 180 formed on the control panel 130 may include a user interface, such as a keyboard 132 including a keypad 133, a mouse, a trackball 131, a time gain compensation (TGC) control knob, a lateral gain compensation (LGC) control knob, a paddle, or the like.

The input 180 may be implemented as the display 121 such that the above-described trackball 131, the TGC control knob, and the like are implemented as user interfaces on the display 121, or such that the keyboard 132, the mouse, the LGC control knob, the paddle, and various buttons, wheels or knobs that may be manipulated by a user are implemented as user interfaces on the display 121.

The control panel 130 may be provided with a separate connection member to be moved with respect to the main body 101. For example, the connection member may be provided as various connection movement devices, such as s a slide, a roller, and a joint, such that the control panel 130 may move in various directions with respect to the main body 101.

The control panel 130 may be moved in various directions with respect to the main body 101 according to a control command of a user.

For example, the control panel 130 may move forward or backward with respect to the ultrasound diagnostic apparatus 100 to become close to or distant away from the user who uses the ultrasound diagnostic apparatus 100. In addition, the control panel 130 may move upward or downward to suit the operation criteria of the user who uses the ultrasound diagnostic apparatus 100, or may move leftward or rightward with respect to the main body 101.

In addition, the control panel 130 may be tilted to adjust the inclination of the control panel 130, and may be provided to be rotatable with respect to the main body 101.

A footrest 140 may be provided at a lower side of the main body 101. The footrest 140 refers to an area on which the user performing the ultrasound diagnosis rests his or her foot. Here, the footrest 140 may be implemented not only as a simple support provided to support the foot of the user, but also as a foot switch or a foot pedal to control various operations of the ultrasonic diagnostic apparatus 100.

The main body 101 may be provided with a controller 160 built into the main body 101. The controller 160 may include at least one memory 162 in which a program for performing an operation described below is stored and at least one processor 161 for executing the stored program.

A plurality of casters 170 for movement of the ultrasound diagnostic apparatus 100 may be provided at a lower side of the main body 101. The user may allow the ultrasound diagnostic apparatus 100 to be fixed or moved using the plurality of casters 170. Such an ultrasonic diagnostic apparatus 100 is referred to as a cart type ultrasonic apparatus.

In addition, the plurality of casters 170 may be controlled by an electrical signal to fix or move the ultrasound diagnostic apparatus 100. That is, the plurality of casters 170, when the user applies an input to move the main body 101, may be moved on the basis of an electric signal according to the user's input, and when the user applies an input to fix the main body 101, may be fixed on the basis of an electric signal corresponding thereto.

In addition, the plurality of casters 170 may be automatically locked to fix the ultrasound diagnostic apparatus 100 according to a control signal of the controller 160 as described below.

Figure 2:
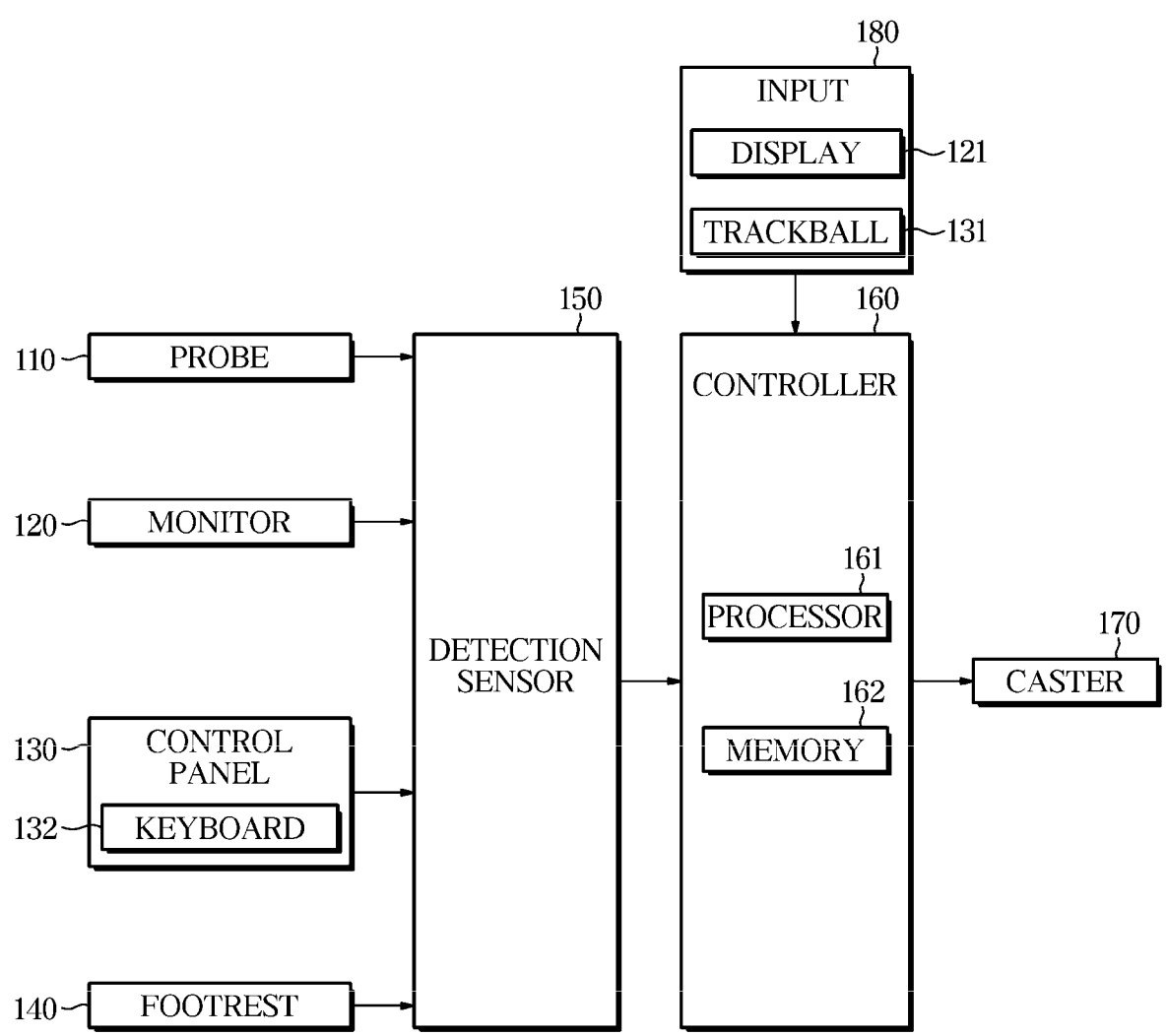
FIG. 2 is a block diagram illustrating an ultrasound diagnostic apparatus according to an embodiment.

FIG. 2 is a block diagram illustrating an ultrasound diagnostic apparatus according to an embodiment.

Referring to FIG. 2, the ultrasound diagnostic apparatus 100 according to the embodiment may include the probe 110 irradiating an ultrasound signal to an object and receiving an ultrasound signal reflected from the object, the control panel 130 including the monitor 120 and the keyboard 132 to control the ultrasound apparatus 100, the footrest 140 on which the foot of the user is rested, a detection sensor 150 that detects a motion of the ultrasound apparatus 100, the input 180 that receives a control command of the ultrasound diagnostic apparatus 100 from the user, the controller 160 that determines whether the user desires to use the ultrasound diagnostic apparatus 100 on the basis of at least one of the motion detected by the detection sensor 150 or the control command received by the input 180 and upon determining that the user desires to use the ultrasound apparatus 100, transmits a control signal for locking at least one of the plurality of casters 170, and the plurality of 170 for movement of the ultrasound diagnostic apparatus 100 according to the control signal.

According to the embodiment, the detection sensor 150 may detect at least one of a position change of the probe 110, a position change of the monitor 120, a position change of the control panel 130, a position change of the keyboard 132, or a position change of the footrest 140.

In detail, the detection sensor 150 may include an acceleration sensor, a gyro sensor, a motion sensor, and a current sensor. The detection sensor 150 is not limited thereto, and may be implemented as various sensors capable of detecting the motion of the ultrasound diagnostic apparatus 100.

For example, the detection sensor 150 may include an acceleration sensor, a gyro sensor, a motion sensor, a pressure sensor, and a current sensor provided in the probe 110, and may be a motion sensor provided in the probe holder 111 to detect the position change of the probe 110.

In addition, the detection sensor 150 may include an acceleration sensor, a gyro sensor, a motion sensor, a pressure sensor, and a current sensor that may be included in the monitor 120, and may detect a position change of the monitor 120.

In addition, the detection sensor 150 may include an acceleration sensor, a gyro sensor, a motion sensor, a pressure sensor, and a current sensor that may be provided in the control panel 130 to detect a position change of the control panel 130.

In addition, the detection sensor 150 may include an acceleration sensor, a gyro sensor, a motion sensor, a pressure sensor, and a current sensor that may be provided in the keyboard 132 to detect a position change of the keyboard 132.

In addition, the detection sensor 150 may include an acceleration sensor, a gyro sensor, a motion sensor, a pressure sensor, and a current sensor that may be provided in the footrest 140 to detect a position change of the footrest 140.

However, the detection sensor 150 is not limited to the above-described sensors, and may be provided as various sensors capable of detecting the motion of the ultrasound diagnostic apparatus 100.

The detection sensor 150 may transmit the detected motion of the ultrasound diagnostic apparatus 100 to the controller 160, and the controller 160 may determine whether the user desires to use the ultrasound diagnostic apparatus 100 on the basis of detected motion.

The controller 160 according to the embodiment may include the processor 161, and may include a read only memory (ROM) in which a program for controlling the ultrasound diagnostic apparatus 100 is stored and a random access memory (RAM) used as a storage area corresponding to various operations performed by the ultrasound imaging apparatus. In addition, the controller 160 may be implemented as a processing board (a graphic processing board) including a circuit board and the processor 161 and the RAM or RAM provided on the circuit board, in which the processor 161 and the RAM and ROM may be connected to each other through an internal bus.

The controller 160 may include at least one memory 162 for memorizing/storing programs and data, and at least one processor 161 for processing data memorized/stored in the memory 162 according to programs memorized/stored in the memory 162. The controller 160 may include hardware, such as the processor 161 and the memory 162 and software, such as programs and data memorized/stored in the memory 162.

The memory 162 may store a program and data for controlling the operation of the ultrasound diagnostic apparatus 100. In detail, the memory 162 may be configured to store instructions executed by the processor 161 and data processed by the instructions. To this end, the memory 162 may include a nonvolatile memory, such as a ROM and a flash memory, for storing data for a long time, and a volatile memory, such as an static random access memory (SRAM) and a dynamic random access memory (DRAM) for temporarily storing data. The memory 162 may store a program and data for controlling the operation of the ultrasound diagnostic apparatus 100. In detail, the memory 162 may be configured to store instructions executed by the processor 161 and data processed by the instructions. To this end, the memory 162 may include a nonvolatile memory, such as a ROM and a flash memory, for storing data for a long time, and a volatile memory, such as an static random access memory (SRAM) and a dynamic random access memory (DRAM) for temporarily storing data.

The caster 170 according to the embodiment may be implemented by an electric method using an electric motor built in a wheel of the caster 170, the steering thereof may also be implemented by an electric method, and the caster 179 may be fixed according to a control signal of the controller 160.

The caster 170 may include a caster body, a wheel, a wheel shaft, a driving motor, a steering motor, and a braking device.

The input 180 according to the embodiment may include user interfaces, such as the keyboard 132, the mouse, the trackball 131, the TGC control knob, the LGC control knob, the paddle, or the like.

In addition, the input 180 may be implemented as the display 121 such that the above-described trackball 131, the TGC control knob, and the like are implemented as a user interface on the display 121, or such that the keyboard 132, the mouse, the LGC control knob, the paddle, and other various buttons, wheels or knobs that may be manipulated by a user are implemented as a user interface on the display 121.

The input 180 according to the embodiment of the disclosure may receive a control command of the ultrasound diagnosis apparatus 100 from a user, and may transmit the received control command to the controller 160. The controller 160 may determine whether the user desires to use the ultrasound diagnostic apparatus 100 on the basis of the received control command.

The controller 160 may determine that the user desires to use the ultrasound diagnostic apparatus 100 when the input 180 receives a diagnosis start command of the ultrasound diagnostic apparatus 100 from the user. The diagnosis start command may include a command for turning on the power of the ultrasound diagnostic apparatus 100.

Hereinafter, a structure and an operation method of the caster 170 will be described with reference to FIG. 3.

Figure 3:
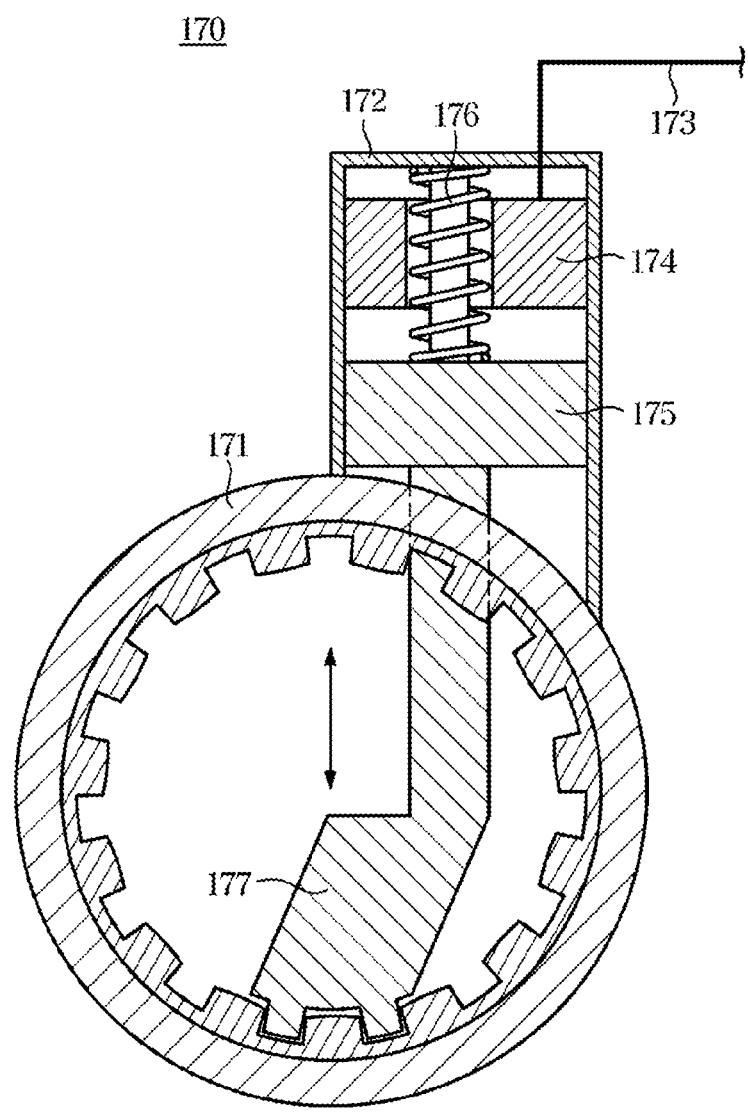
FIG. 3 is a view for describing a structure and an operation method of a caster according to an embodiment.

FIG. 3 is a view for describing the structure and the operation method of the caster 170 according to the embodiment.

Referring to FIG. 3, the caster 170 according to the embodiment may include a wheel 171 for moving the ultrasonic diagnostic apparatus 100, a housing 172 accommodating each component of the caster 170, a circuit 173 for receiving a control signal transmitted by the controller 160, an electromagnet 174 magnetized in response to current flowing thereto, and demagnetized in response to current interrupted and returning to its original state, a plunger 175 forced in a direction that is same as or opposite to a direction of the electromagnet 174 according to the magnetism of the electromagnet 174, a spring 176 that is compressed or extended in accordance with the direction of the force exerted on the plunger 175, and a brake 177 allowing the wheel 171 to be locked when the plunger is forced in a direction opposite to that of the electromagnet 174.

When a current flows through the circuit 173, the electromagnet 174 is magnetized, and an attraction force of the electromagnet 174 acts on the plunger 175 such that the plunger 175 may be forced in the direction of the electromagnet 174. At this time, the spring 176 may be compressed according to the force exerted on the plunger 175, and the plunger 175 may be lifted as the spring 176 is compressed. When the plunger 175 is lifted, the brake 177 may be lifted such that the wheel 171 may be unlocked. That is, when the current flows through the circuit 173, the caster 170 may be kept unlocked.

When no current flows through the circuit 173, the electromagnet 174 is not magnetized and no force is exerted on the plunger 175. At this time, the plunger 175 may be forced in a direction opposite to the direction of the electromagnet 174 (forced in the downward direction) by the elastic force (restoration force) of the spring 176 and thus may be lowered. When the plunger 175 is lowered, the brake 177 is lowered such that the wheel 171 may be locked. That is, when no current flows through the circuit 173, the caster 170 may be kept locked.

As described above, the caster 170 may be locked according to the control signal of the controller 160. For example, when the controller 160 transmits a control signal to lock the caster 170, the control signal may be transmitted to the electromagnet 174 through the circuit 173, and the plunger 175 Is lowered according to the control signal, and the brake 177 is lowered in accordance with the lowering of the plunger 175 such that the wheel 171 is fixed without being moved. In this case, the control signal of the controller 160 may be a signal for preventing current from flowing in the circuit 173.

The above described structure and operation method of the caster is merely one example, and the control signal of the controller 160 may variously implemented according to the structure of the brake 177, and the positions of the electromagnet 174, the plunger 175, the spring 176, and other components of the caster. Hereinafter, a process of automatically locking the caster 170 of the ultrasound diagnostic apparatus 100 will be described with reference to FIGS. 4 to 9.

FIGS. 4 to 9 are diagrams for describing a process in which the caster 170 of the ultrasound diagnostic apparatus 100 is automatically locked according to the embodiment, in which the controller 160 determines whether the user desires to use the ultrasound diagnostic apparatus 100 on the basis of at least one of a motion detected by the detection sensor 150 and a control command received by the input 180. In other words, the controller 160 may determine whether the user intends to use the ultrasound diagnostic apparatus 100 on the basis of the motion detected by the detection sensor 150 or the control command received by the input 180.

Figure 4:
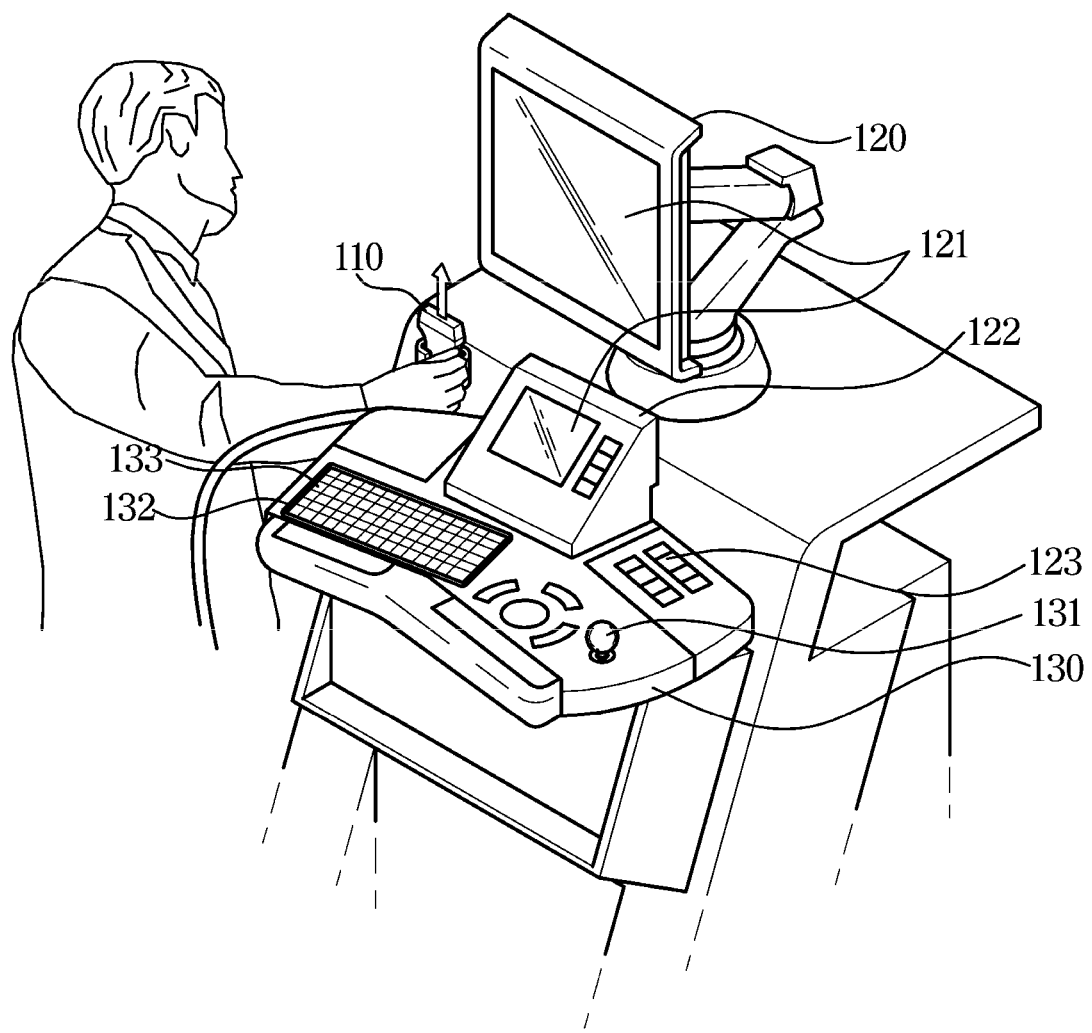
FIGS. 4 to 9 are diagrams for describing a process in which a caster of an ultrasound diagnostic apparatus is automatically locked according to an embodiment.

FIG. 4 illustrates a case in which the user selects and detaches the probe 110 to use the ultrasound diagnostic apparatus 100.

Referring to FIG. 4, in the process of the user selecting and detaching the probe 110, the detection sensor 150 may detect a change in the position of the probe 110.

In detail, the detection sensor 150 may be an acceleration sensor, a gyro sensor, or a motion sensor provided in the probe 110, and may detect an acceleration, tilt, or motion of the probe 110 to detect a change in the position of the probe 110. In addition, the detection sensor 150 may be a current sensor for detecting a current generated by the motion of the probe 110, and in this case, the detection sensor 150 may detect a change in the position of the probe 110 by sensing a current.

In general, when the user generates a change in the position of the probe 110, it is logically determined that the user has an intention of using the ultrasound diagnostic apparatus 100.

Therefore, in response to detecting a change in the position of the probe 110, the controller 160 may determine that the user desires to use the ultrasound diagnostic apparatus 100. In response to determining that the user desires to use the ultrasound diagnostic apparatus 100, the controller 160 may transmit a control signal for locking at least one of the plurality of casters 170, and the plurality of casters 170 may be automatically locked according to the control signal of the controller 160.

When the user finishes using the ultrasound diagnostic apparatus 100 and mounts the probe 110 on the probe holder 111 again, the controller 160 may transmit a control signal for unlocking the plurality of casters 170, and in preparation for the user to use the ultrasound diagnostic apparatus 100 again, may transmit the control signal for unlocking the plurality of casters 170 after a predetermined time since the probe 110 is mounted on the probe holder 111.

In this case, the predetermined time may be set as an appropriate time enough to determine that the user does not desire to use the probe 110, and may be set, for example, according to a user's input.

Figure 5:
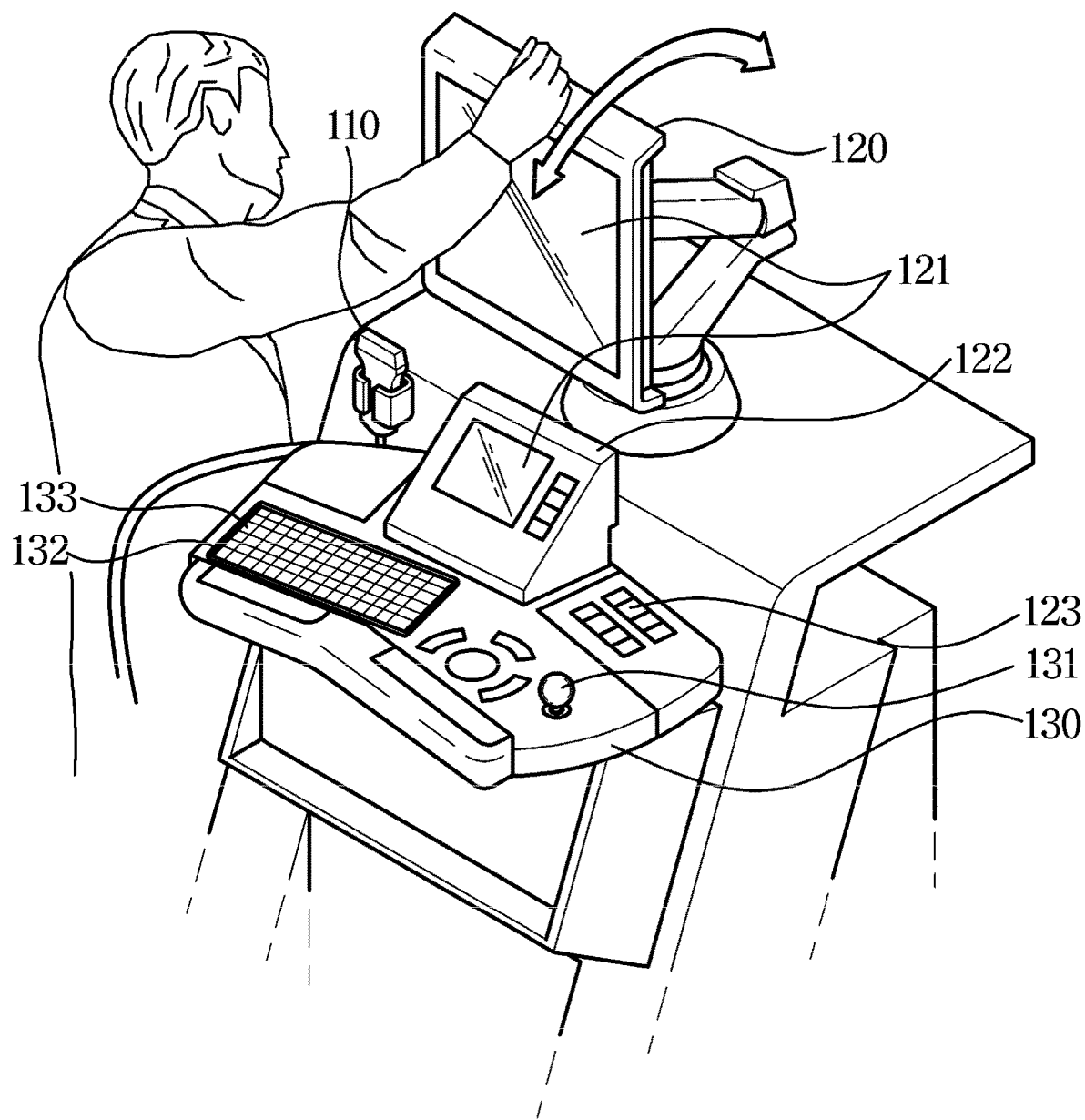

FIG. 5 illustrating a case in which the user changes the position of the monitor 120 to use the ultrasound diagnostic apparatus 100.

Referring to FIG. 5, when the user adjusts the position of the monitor 120 to use the monitor 120, the detection sensor 150 may detect a change in the position of the monitor 120. In addition, when a user inputs a unlock command for adjusting the position of the monitor 120 to the input 180, the control command may be transmitted to the controller 160. The input 180 may be, for example, a separate button 123 provided on the control panel 130.

In detail, the detection sensor 150 may be an acceleration sensor, a gyro sensor, or a motion sensor provided in the monitor 120, and may detect an acceleration, tilt, or motion of the monitor 120 to detect a change in the position of the monitor 120. In addition, the detection sensor 150 may be a current sensor for detecting a current generated by the motion of the monitor 120, and in this case, the detection sensor 150 may detect a change in the position of the monitor 120 by sensing a current.

In addition, the input 180 may receive a current or pressure generated when the unlock command for changing the position of the monitor 120 is input, and transmit the received current or pressure to the controller 160. For example, when a user presses the button 123 provided on the control panel 130 to unlock the monitor 120, the input 180 generates a control command by sensing a pressure applied to the button 123 or using current generated by the pressing of the button 123, and transmit the control command to the controller 160.

When the unlock command for changing the position of the monitor 120 is input to the input 180, or when a change in the position of the monitor 120 is detected by the detection sensor 150, the controller 160 determines that the user desires to the ultrasound diagnostic apparatus 100. When it is determined that the user desires to use the ultrasound diagnostic apparatus 100, the controller 160 may transmit a control signal for locking at least one of the plurality of casters 170, and the plurality of casters 170 may be automatically locked according to the control signal.

When the user finishes using the ultrasound diagnostic apparatus 100 and inputs a lock command for securing the position of the monitor 120, the controller 160 may transmit a control signal for unlocking the plurality of casters 170, and in preparation for the user to use the ultrasound diagnostic apparatus 100 again, may transmit the control signal for unlocking the plurality of casters 170 after a predetermined time since the lock command for the monitor 120 is input.

In this case, the predetermined time may be set as an appropriate time enough to determine that the user does not desire to use the monitor 120, and may be set, for example, according to a user's input.

Figure 6:
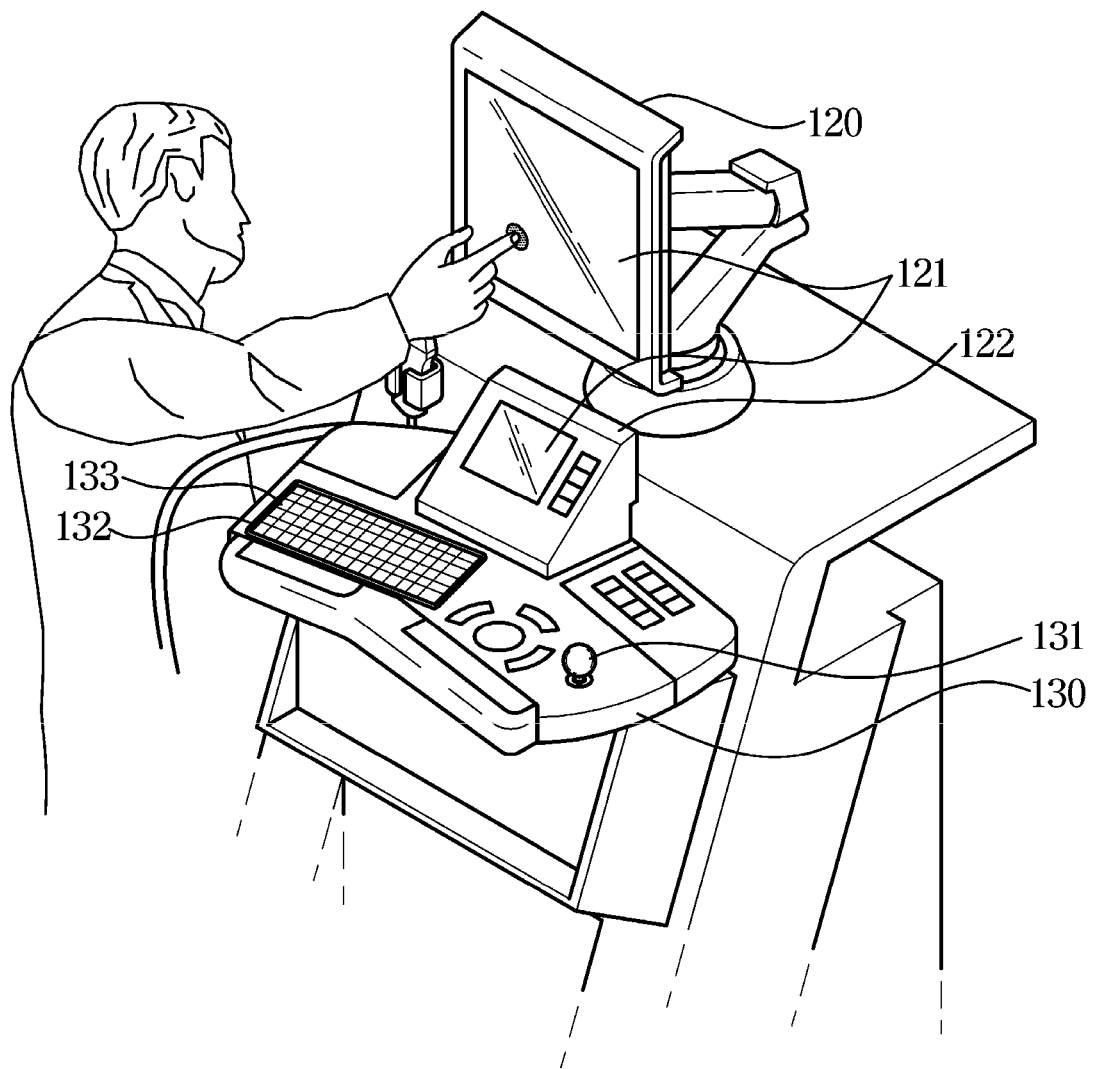

FIG. 6 is a view illustrating a case in which a user inputs a control command to the display 121 to use the ultrasound diagnostic apparatus 100.

Referring to FIG. 6, a user may input a control command to the display 121 to use the ultrasound diagnostic apparatus 100. The display 121 may be provided in the monitor 120, but the location thereof is not limited thereto as long as it can receive an input from the user.

In addition, the control command input by the user to the display 121 may be, for example, an input for unlocking the display 121. That is, when the user does not use the ultrasound diagnostic apparatus 100, the display 121 is automatically locked, and in order for the ultrasound diagnostic apparatus 100 to be used, the user needs to unlock the display 121, for example, by touching the display 121. In this case, the display 121 may be implemented as a touch screen.

When the control command is input to the display 121, the controller 160 may determine that the user desires to use the ultrasound diagnostic apparatus 100. When it is determined that the user desires to use the ultrasound diagnostic apparatus 100, the controller 160 may transmit a control signal for locking at least one of the plurality of casters 170, and the plurality of casters 170 may be automatically locked according to the control signal.

Figure 7:
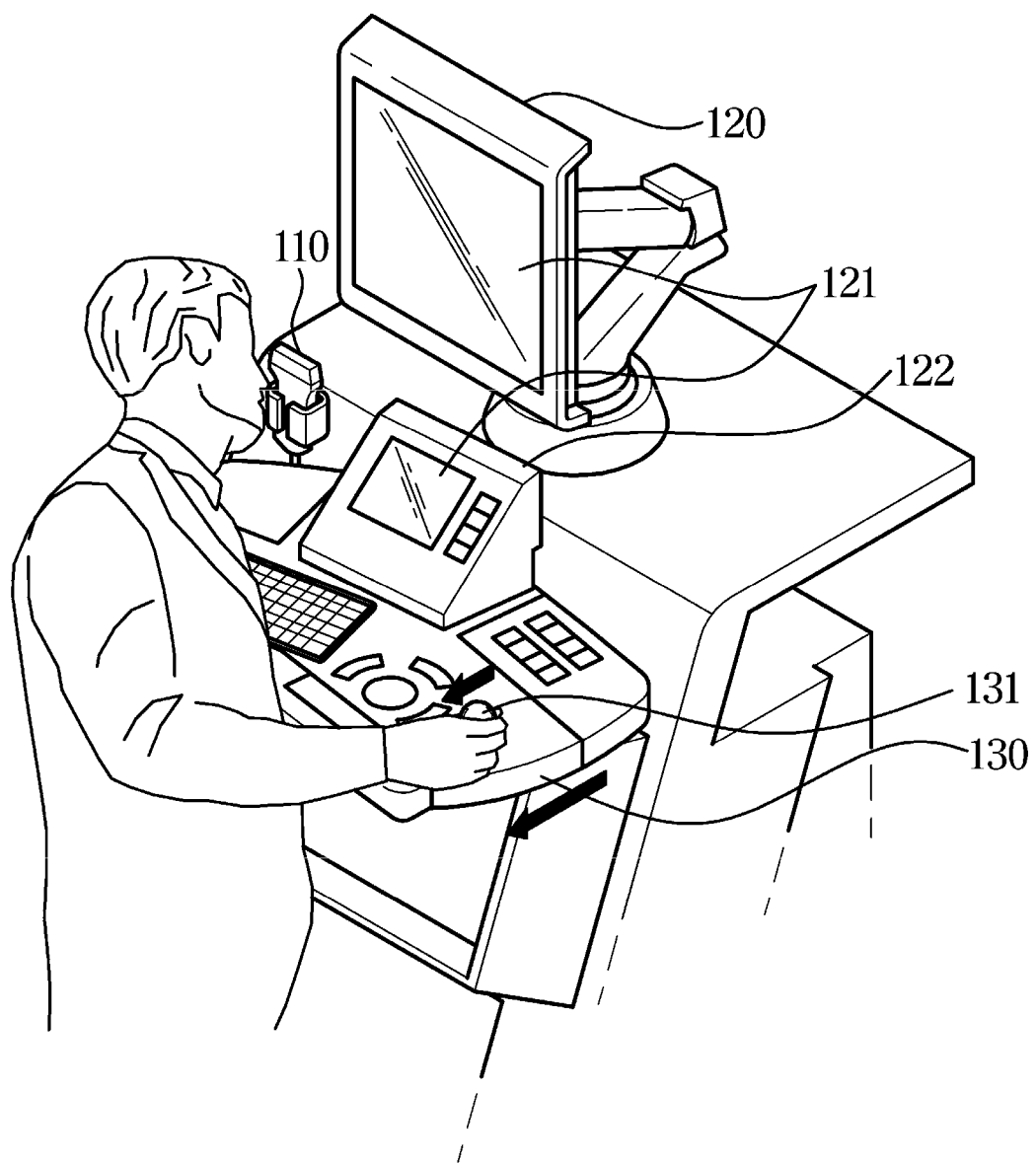

FIG. 7 is a diagram illustrating a case in which the user adjusts the position of the control panel 130 to use the ultrasound diagnostic apparatus 100.

Referring to FIG. 7, when the user adjusts the position of the control panel 130 to use the ultrasound diagnostic apparatus 100, the detection sensor 150 may detect a change in the position of the control panel 130.

In detail, the detection sensor 150 may be an acceleration sensor, a gyro sensor, or a motion sensor provided in the control panel 130, and may detect an acceleration, tilt, or motion of the control panel 130 to detect a change in the position of the control panel 130. In addition, the detection sensor 150 may be a current sensor for detecting a current generated by the motion of the control panel 150, and in this case, the detection sensor 150 may detect a change in the position of the control panel 130 by sensing a current.

In addition, referring to FIG. 7, when a user inputs a command to the trackball 131 to adjust the position of the control panel 130, the trackball 131 may transmit the received control command to the controller 160. That is, the control command input by the user to the trackball 131 may be a command for adjusting the position of the control panel 130.

In addition, when the user does not use the ultrasound diagnostic apparatus 100, the display 121 is automatically locked, and in order for the ultrasound diagnostic apparatus 100 to be used, the user may unlock the display 121, for example, by moving the trackball 131. In this case, the control command input by the user to the trackball 131 may be a command for unlocking the display 121.

In general, when the user generates a change in the position of the control panel 130 or inputs a control command to the trackball 131, it is logically determined that the user has an intention of using the ultrasound diagnostic apparatus 100.

Therefore, in response to the detection sensor 150 detecting a change in the position of the control panel 130 or in response to the trackball 131 receiving a control command, the controller 160 may determine that the user desires to use the ultrasound diagnostic apparatus 100. In response to determining that the user desires to use the ultrasound diagnostic apparatus 100, the controller 160 may transmit a control signal for locking at least one of the plurality of casters 170, and the plurality of casters 170 may be automatically locked according to the control signal of the controller 160.

Figure 8:
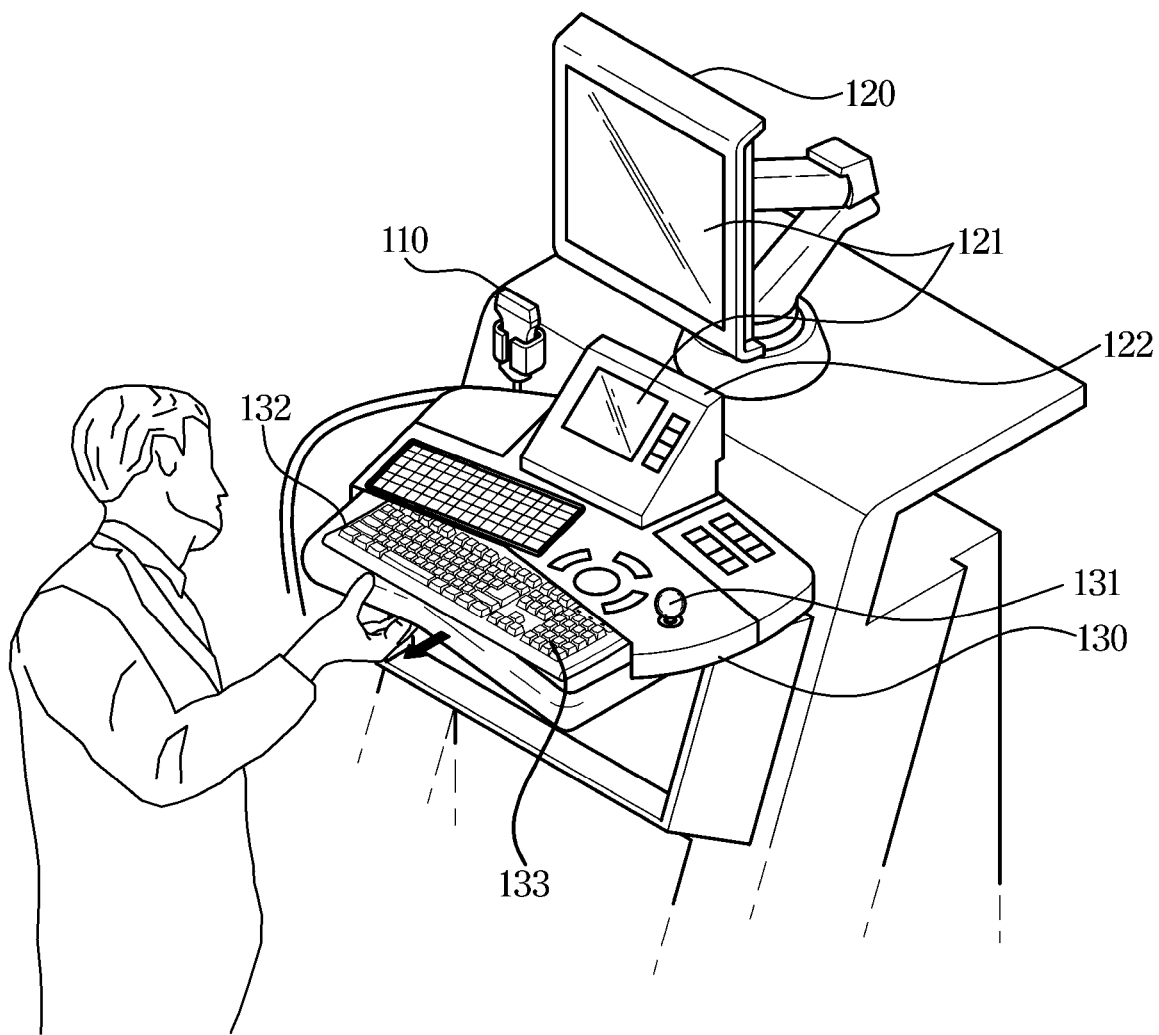

FIG. 8 is a diagram illustrating a case in which a user adjusts the position of the keyboard 132 or inputs a command to the keypad 133 to use the ultrasound diagnostic apparatus 100.

Referring to FIG. 8, the keyboard 132 may be provided in a buried type keyboard buried in the bottom of the control panel 130, and when the user withdraws a keyboard holder to use the keyboard 132, a change in the position of the keyboard 132 is detected by the detection sensor 150.

In detail, the detection sensor 150 may be an acceleration sensor, a gyro sensor, or a motion sensor provided in the keyboard holder or the keyboard 132, and may detect an acceleration, tilt, or motion of the keyboard 132, to detect a change in the position of the keyboard 132. In addition, the detection sensor 150 may be a current sensor for detecting a current generated by the motion of the keyboard 132 or the keyboard holder, and in this case, the detection sensor 150 may detect a change in the position of the keyboard 132 by sensing a current.

In addition, when the user inputs a control command to the keypad 133, the input 180 may transmit the control command to the controller 160. That is, when the user does not use the ultrasound diagnostic apparatus 100, the display 121 is automatically locked, and in order for the ultrasound diagnostic apparatus 100 to be used, the user needs to unlock the display 121, for example, by inputting an input to the keypad 133. In this case, the control command input by the user to the keypad 133 may be a command for unlocking the display 121.

In general, when the user generates a change in the position of the keyboard 132, it is logically determined that the user has an intention of using the ultrasound diagnostic apparatus 100.

Therefore, in response to the detection sensor 150 detecting a change in the position of the keyboard 132 or in response to the keypad 133 receiving a control command, the controller 160 may determine that the user desires to use the ultrasound diagnostic apparatus 100. In response to determining that the user desires to use the ultrasound diagnostic apparatus 100, the controller 160 may transmit a control signal for locking at least one of the plurality of casters 170, and the plurality of casters 170 may be automatically locked according to the control signal of the controller 160.

When the user finishes using the ultrasound diagnostic apparatus 100 and returns the keyboard holder to its original position, the controller 160 may transmit a control signal for unlocking the plurality of casters 170, and in preparation for the user to use the ultrasound diagnostic apparatus 100 again, may transmit the control signal for unlocking the plurality of casters 170 after a predetermined time since the keyboard 132 is returned to its original state.

In this case, the predetermined time may be set as an appropriate time enough to determine that the user does not desire to use the ultrasound diagnostic apparatus 110, and may be set, for example, according to a user's input.

Figure 9:
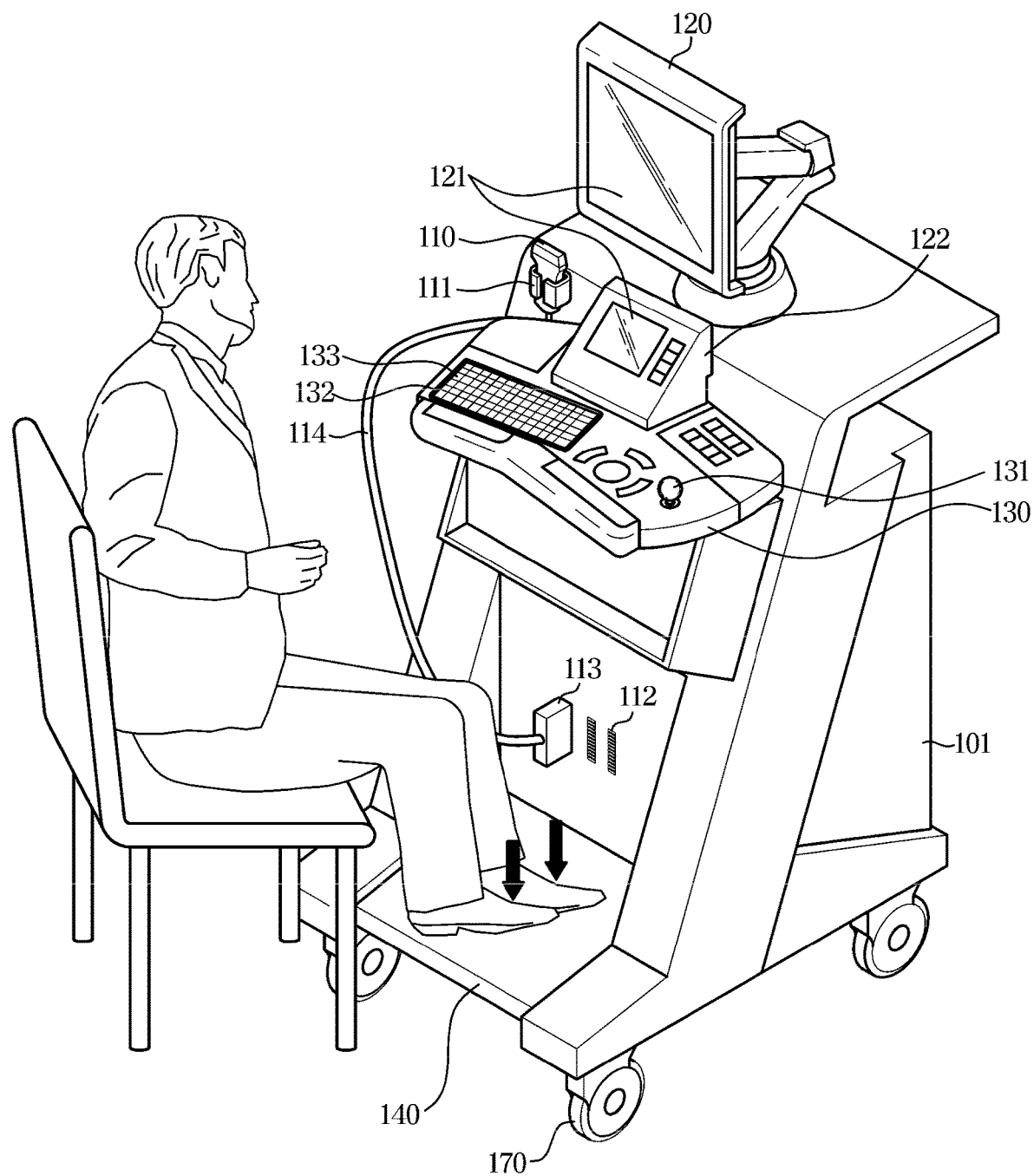

FIG. 9 is a diagram illustrating a case in which a user rests his or her foot on the footrest 140 to use the ultrasound diagnostic device 100.

Referring to FIG. 9, when the user rests the foot on the footrest 140 while using the ultrasound diagnostic apparatus 100, the detection sensor 150 may detect a change in the position of the footrest 140.

In addition, the detection sensor 150 may be an acceleration sensor, a gyro sensor, or a motion sensor provided in the footrest 140, and may detect an acceleration, tilt, or motion of the footrest 140 to detect a change in the position of the footrest 140. In addition, the detection sensor 150 may be a current sensor for detecting a current generated by the motion of the footrest 140, and in this case, the detection sensor 150 may detect a change in the position of the footrest 140 by sensing a current.

In general, when the user generates a change in the position of the footrest 140, it is logically determined that the user has an intention of using the ultrasound diagnostic apparatus 100.

Therefore, in response to detecting a change in the position of the footrest 140, the controller 160 may determine that the user desires to use the ultrasound diagnostic apparatus 100. In response to determining that the user desires to use the ultrasound diagnostic apparatus 100, the controller 160 may transmit a control signal for locking at least one of the plurality of casters 170, and the plurality of casters 170 may be automatically locked according to the control signal of the controller 160.

When the user finishes using the ultrasound diagnostic apparatus 100 and removes the foot from the footrest 140, the controller 160 may transmit a control signal for unlocking the plurality of casters 170, and in preparation for the user to use the ultrasound diagnostic apparatus 100 again, may transmit the control signal for unlocking the plurality of casters 170 after a predetermined time since the user removes the foot from the footrest 140.

In this case, the predetermined time may be set as an appropriate time enough to determine that the user does not desire to use the ultrasound diagnostic apparatus 100, and may be set, for example, according to a user's input.

As described above, the controller 160 may determine whether the user desires to use the ultrasound diagnostic apparatus 100 on the basis of at least one of a motion detected by the detection sensor 150 and a control command received by the input 180. However, the above description is only an embodiment of the disclosure, and the disclosure may transmit a control signal for locking at least one of the plurality of casters 170 also by other motions of the ultrasound diagnostic apparatus 100 or other control commands input to the input 180 including a user's intention of using the ultrasound apparatus 100.

In addition, according to a user's setting received from the input 180 or the memory 162 stored in the controller 160, the controller 160 may configured to, in response to sensing two or more motions of the ultrasound diagnostic apparatus 100 or receiving two or more control commands input to the input 180 including a user's intention of using the ultrasound apparatus 100, may determine that the user desires to use the ultrasound diagnostic apparatus 100 and may transmit a control signal for locking at least one of the plurality of casters 170. Accordingly, the caster 170 is prevented from being automatically locked by an inadvertent motion of the ultrasound diagnostic apparatus 100 or an inadvertent control command received by the input 180.

Hereinafter, a process of unlocking the caster 170 of the ultrasound diagnostic apparatus 100 or setting an auto lock function as an option will be described with reference to FIGS. 10 and 11.

Figure 10:
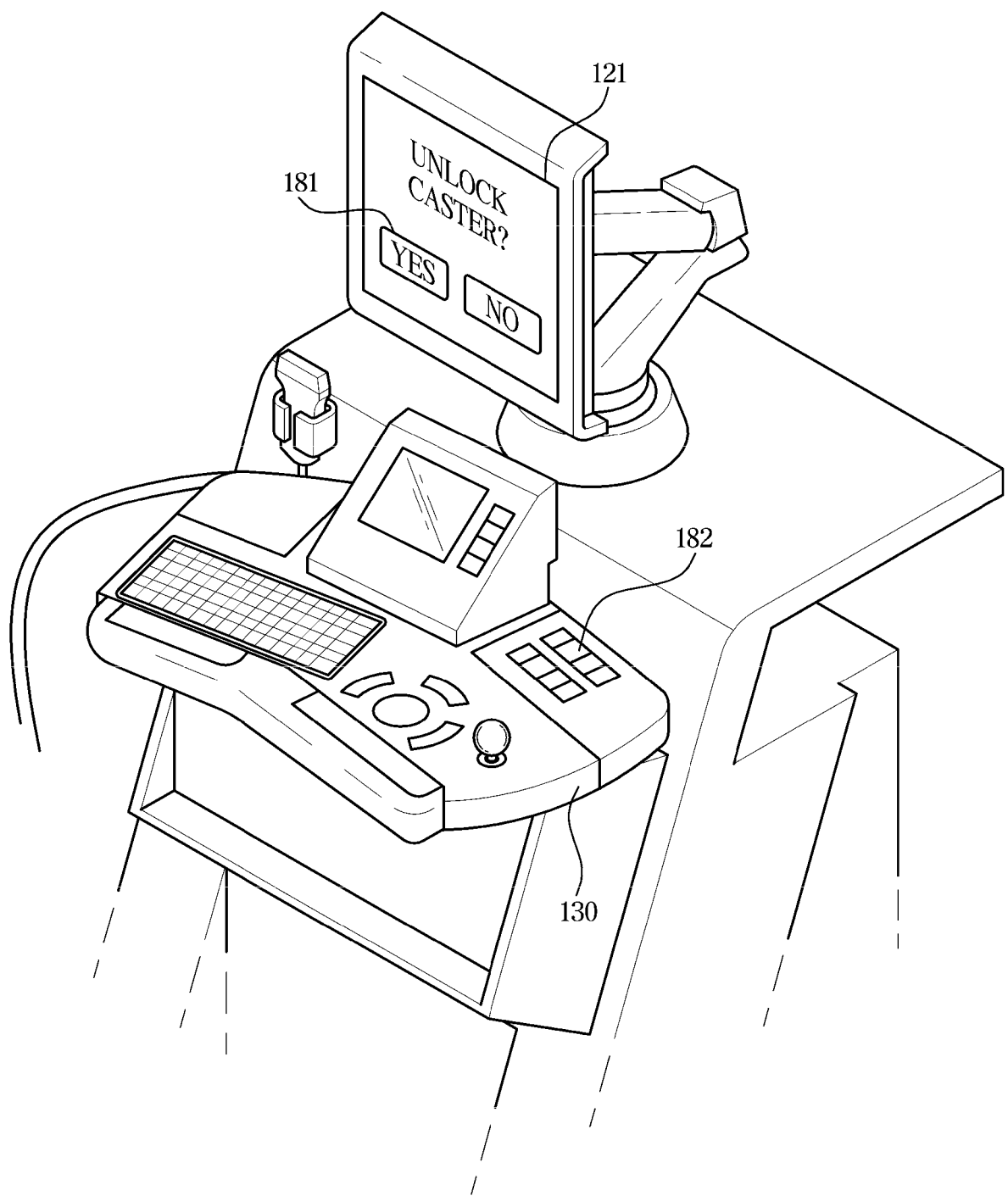
FIG. 10 is a diagram for describing a process in which a caster of an ultrasound diagnostic apparatus is unlocked according to an embodiment.

FIG. 10 is a diagram for describing a process in which a caster of an ultrasound diagnostic apparatus is unlocked according to an embodiment.

Referring to FIG. 10, the input 180 of the ultrasound diagnostic apparatus 100 may receive a unlock command of the caster 170 from a user.

The input 180 as illustrated in FIG. 10 may be a touch screen of the display 121 into which a user may input a command by a touch operation, or may be a separate button 182 provided on the control panel 130.

However, the input 180 is not limited to the touch screen of the display 121 or the separate button 182, and it should be understood that the input 180 may include all types of components that may receive a user's command.

Referring again to FIG. 10, in order to unlock the caster 170 that is automatically locked, the user may touch an unlock button 181 displayed on the display 121, or press the separate button 182 provided on the control panel 130 to input an unlock command.

When the unlock command is input, the controller 160 may transmit a control signal to unlock the caster 170.

Figure 11:
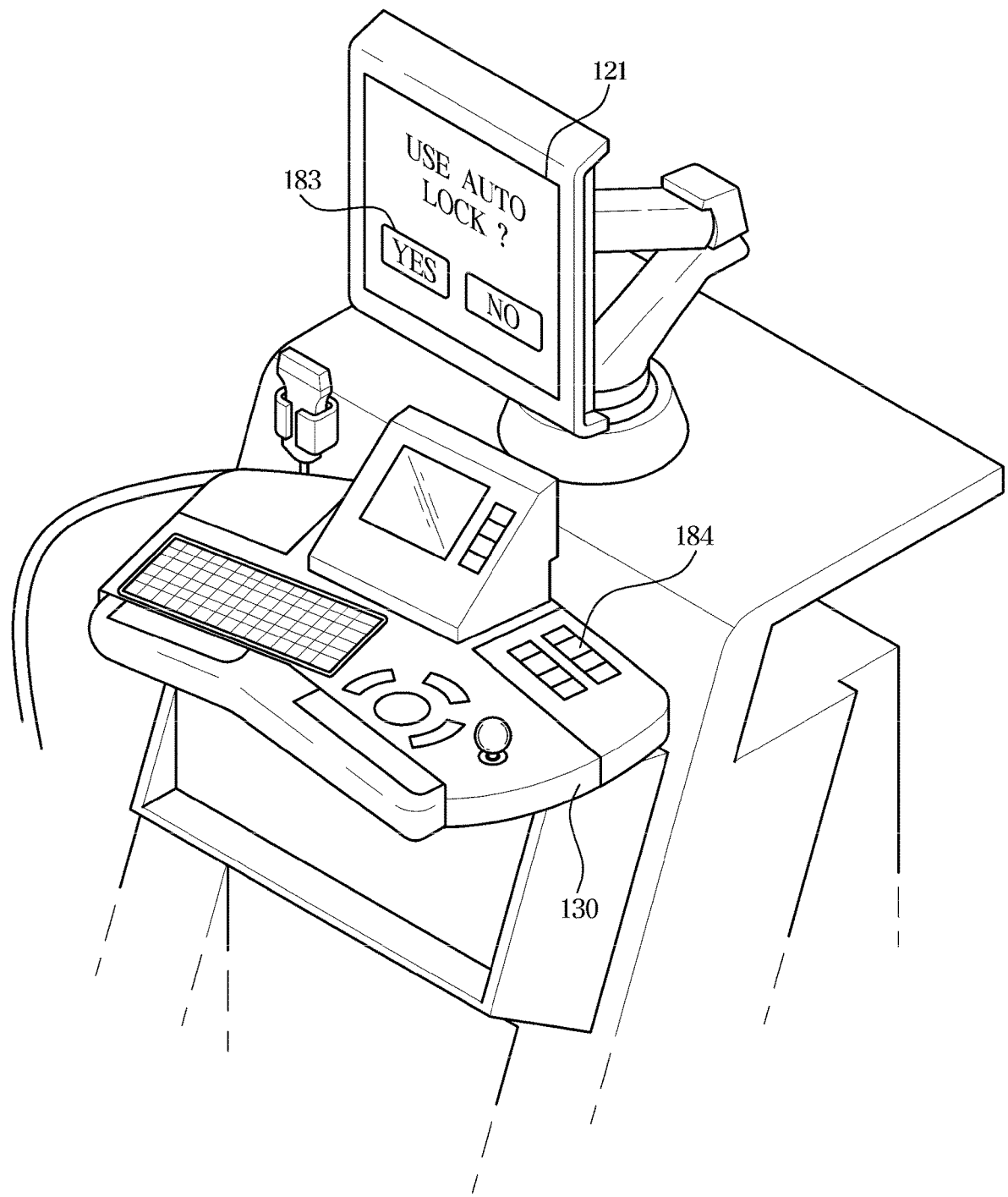
FIG. 11 is a diagram for describing a process in which an auto lock function of an ultrasound diagnostic apparatus is canceled according to an embodiment.

FIG. 11 is a diagram for describing a process in which an auto lock function of an ultrasound diagnostic apparatus is cancelled according to an embodiment.

Referring to FIG. 11, the ultrasound diagnostic apparatus 100 may include the input 180 that receives a command for activating or deactivating the auto lock function of the caster 170 from a user.

Referring to again FIG. 11, the input 180 may be a display 112 into the user may input a command through a touch operation or a separate button 184 provided on the control panel 130. However, the input 180 is limited thereto, and it should be understood that the input 180 may include all types of components that may receive user commands.

Referring again to FIG. 11, in order to activate an auto lock function of the caster 170, the user may touch an auto lock activation button 183 displayed on the display 121 or press the separate button 184 provided on the control panel 130 to input a command for activating the auto lock function.

In a state in which the command for activating the auto lock function is input, the controller 160, in response to determining that the user desires to use the ultrasound diagnostic apparatus 100, may transmit a control signal for locking at least one of the plurality of casters 170.

In addition, in order to deactivate the auto lock function of the caster 170, the user may touch a button for deactivating the auto lock function that is displayed on the display 121, and in a state in which a command for deactivating the auto lock function is input by the touching of the button, the controller 160 may not transmit a control signal for locking at least one of the plurality of casters 170 even when it is determined that the user desires to use the ultrasound diagnostic apparatus 100.

As such, the user may optionally set the auto lock function, so that the convenience of the user is improved.

Hereinafter, a method of controlling the ultrasound diagnostic apparatus 100 according to an embodiment will be described with reference to FIG. 12.

Figure 12:
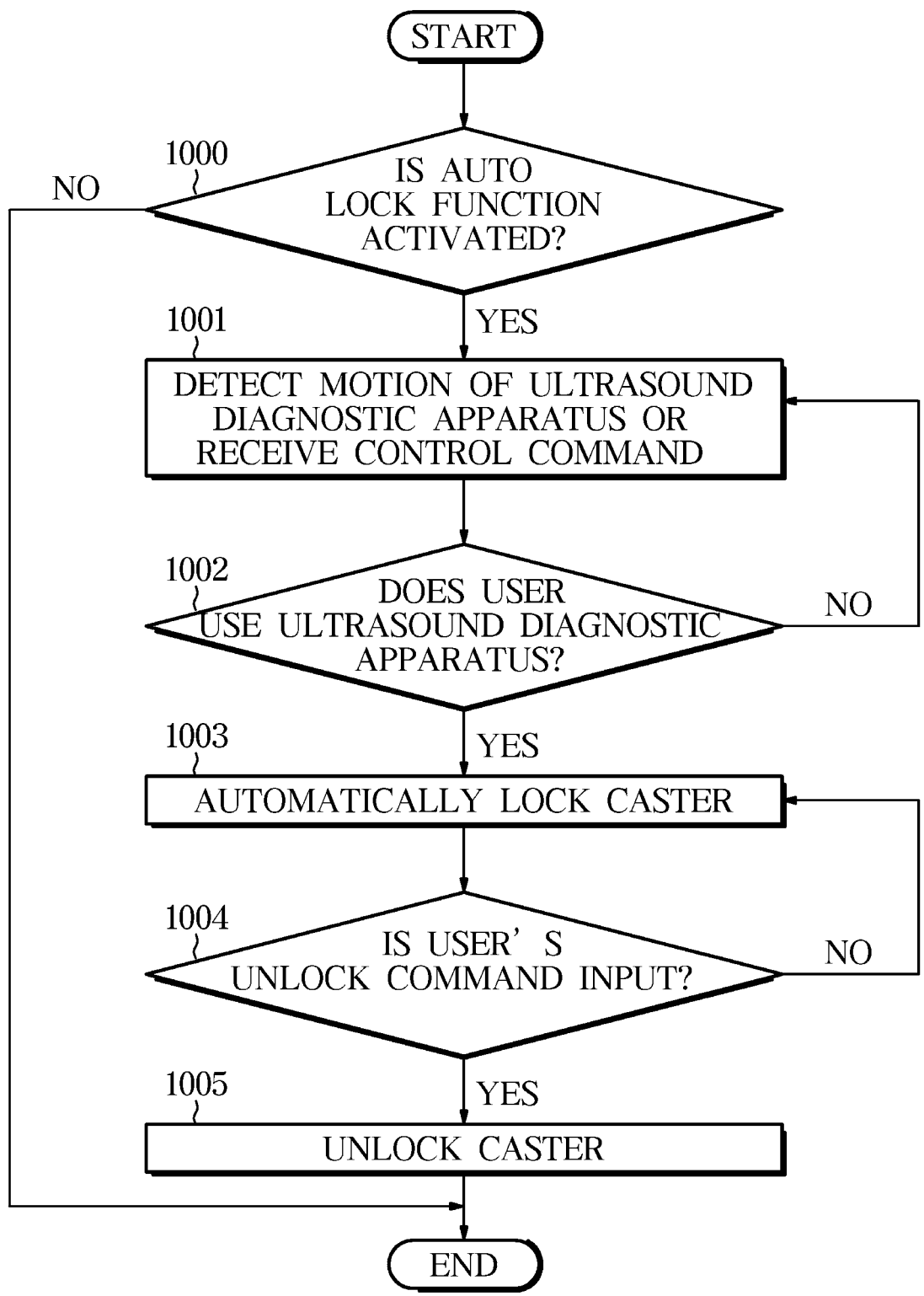
FIG. 12 is a flowchart showing a method of controlling an ultrasound diagnostic apparatus according to an embodiment.

FIG. 12 is a flowchart showing a method of controlling an ultrasound diagnostic apparatus according to an embodiment.

Referring to FIG. 12, the method of controlling the ultrasound diagnostic apparatus 100 according to the embodiment includes receiving a command for activating or deactivating an auto lock function of the caster 170 from a user (1000).

Upon receiving a command for deactivating the auto lock function from the user, the method is terminated without an additional control process, and upon receiving a command for activating the auto lock function, the detection sensor 150 detects a user's operation or input.

It should be understood that regardless of the command for activating or deactivating the auto lock function input from the user, the detection sensor 150 may continuously detect the motion of the ultrasonic diagnostic apparatus, and the input 180 may receive a control command from the user, and in this case, the controller 160 may not transmit a control signal for locking at least one of the plurality of casters 170 even when it is determined that the user desires to use the ultrasound diagnostic apparatus 100.

That is, the operation 1000 of determining whether the auto lock function is activated may be executed before the operation 1002 of determining whether the user desires to use the ultrasound diagnostic apparatus 100.

The method of controlling the ultrasound diagnostic apparatus 100 according to the embodiment includes, when the auto lock function is activated, detecting a motion of the ultrasound diagnostic apparatus 100 or receiving a control command (1001). The detecting of the motion of the ultrasound diagnostic apparatus 100 may be performed by various types of detection sensors 150, and the receiving of the control command of the ultrasound diagnostic apparatus 100 may be performed by the input 180 described above.

When a motion of the ultrasound diagnostic apparatus 100 is detected or a control command is received, the controller 160 may determine whether the user desires to use the ultrasound diagnostic apparatus 100 on the basis of the detected motion or the received control command (1002). That is, whether the user desires to use the ultrasound diagnostic apparatus 100 may be determined on the basis of the motion of the ultrasound diagnostic apparatus 100 or the received control command.

The controller 160, in response to not determining that the user desires to use the ultrasound diagnostic apparatus 100, does not transmit any control signal, and the detection sensor 150 continuously detects a motion of the ultrasound diagnostic apparatus 100, and the input 180 receives an input of a control command of the user.

The controller 160, in response to determining that the user desires to use the ultrasound diagnostic apparatus 100, may transmit a control signal for locking at least one of the plurality of casters 170 such that the caster 170 is automatically locked (1003).

Thereafter, the controller 160 determines whether an unlock command is input from the user through the input 180 (1004), and in response to not receiving the unlock command from the user, keeps the caster 170 in a locked state.

The controller 160, in response to receiving an unlock command from the user may transmit a control signal for unlocking the caster 170 to unlock the caster 170 (1005).

As is apparent from the above, the ultrasound diagnostic apparatus and the method of controlling the same can minimize an unneeded manipulation of the ultrasound diagnostic apparatus and prevent an accident due to an unintended movement of the ultrasound diagnostic apparatus by automatically locking casters of the ultrasound diagnostic apparatus to prevent the ultrasound diagnostic apparatus from being moved when the user performs a diagnostic activity using the ultrasound diagnostic apparatus.

What is claimed is:

1. An ultrasound diagnostic apparatus comprising:
   a plurality of casters configured to be switched to a locking state or an unlocking state;
   an ultrasound probe configured to irradiate an ultrasound signal to an object and receive an echo signal reflected from the object;
   at least one sensor configured to detect an operation of the ultrasound probe; and
   a controller configured to control the plurality of casters in the unlocking state to be in the locking state in response to the operation of the ultrasound probe being detected by the at least one sensor while an auto lock function of the ultrasound diagnostic apparatus is being activated,
   wherein while the auto lock function of the ultrasound diagnostic apparatus is being deactivated, the controller is further configured to control the plurality of casters in the unlocking state to maintain the unlocking state even if the operation of the ultrasound probe is detected by the at least one sensor.

2. The ultrasound diagnostic apparatus of claim 1, wherein the at least one sensor comprises a current sensor configured to detect a current generated according to the operation of the ultrasound probe.

3. The ultrasound diagnostic apparatus of claim 1, wherein the at least one sensor comprises a pressure sensor provided in the ultrasound probe.

4. The ultrasound diagnostic apparatus of claim 1, wherein the controller is further configured to control the plurality of casters in the unlocking state to be in the locking state based on receiving a user input for starting diagnosis while the auto lock function is being activated.

5. The ultrasound diagnostic apparatus of claim 1, wherein the controller is further configured to control the plurality of casters in the unlocking state to be in the locking state based on receiving a user input by at least one input device of the ultrasound diagnostic apparatus while the auto lock function is being activated.

6. The ultrasound diagnostic apparatus of claim 5, wherein the at least one input device comprises at least one of a touch panel, a track ball, a keyboard, a foot switch, a mouse, a knob, or a paddle.

7. The ultrasound diagnostic apparatus of claim 1, wherein the controller is further configured to control the plurality of casters in the locking state to be in the unlocking state when a predetermined time elapsed after the operation of the ultrasound probe being detected by the at least one sensor.

8. The ultrasound diagnostic apparatus of claim 1, wherein each of the plurality of casters comprises a wheel and a locking device configured lock the wheel, wherein the controller is configured to control the locking device to lock the wheel based on the plurality of wheels being in the locking state.

9. The ultrasound diagnostic apparatus of claim 1, wherein each of the plurality of casters comprises a wheel and a motor configured to rotate the wheel, wherein the controller is configured not to drive the motor based on the plurality of wheels being in the locking state.

10. The ultrasound diagnostic apparatus of claim 1, wherein the controller is further configured to control the plurality of casters in the locking state to be in the unlocking state based on receiving a user input for unlocking the plurality of casters.

11. The ultrasound diagnostic apparatus of claim 1, wherein the controller is further configured to:
activate the auto lock function in response to receiving a first user input, and deactivate the auto lock function in response to receiving a second user input.

12. The ultrasound diagnostic apparatus of claim 11, further comprising a first input device configured to receive the first user input, and a second input device configured to receive the second user input.

13. A method of controlling an ultrasound diagnostic apparatus comprising a plurality of casters configured to be switched to a locking state or an unlocking state and at least one sensor configured to detect an operation of an ultrasound probe of the ultrasound diagnostic apparatus, the method comprising:
controlling the plurality of casters in the unlocking state to be in the locking state in response to the operation of the ultrasound probe being detected by the at least one sensor while an auto lock function of the ultrasound diagnostic apparatus is being activated; and
while the auto lock function of the ultrasound diagnostic apparatus is being deactivated, controlling the plurality of casters in the unlocking state to maintain the unlocking state even if the operation of the ultrasound probe is detected by the at least one sensor.

14. The method of claim 13, further comprising controlling the plurality of casters in the unlocking state to be in the locking state based on receiving a user input for starting diagnosis while the auto lock function is being activated.

15. The method of claim 13, further comprising to controlling the plurality of casters in the unlocking state to be in the locking state based on receiving a user input by at least one input device of the ultrasound diagnostic apparatus while the auto lock function is being activated.

16. The method of claim 13, further comprising controlling the plurality of casters in the locking state to be in the unlocking state when a predetermined time elapsed after the operation of the ultrasound probe being detected by the at least one sensor.

17. The method of claim 13, further comprising:
activating the auto lock function in response to receiving a first user input; and
deactivating the auto lock function in response to receiving a second user input.

18. The method of claim 17, wherein the ultrasound diagnostic apparatus further comprises a first input device configured to receive the first user input, and a second input device configured to receive the second user input.

* * * * *